(12) United States Patent
Daniels et al.

(10) Patent No.: US 12,109,378 B2
(45) Date of Patent: Oct. 8, 2024

(54) DIGITAL EXTERNAL VENTRICULAR DRAIN WITH INTEGRATED INTRACRANIAL PRESSURE MONITOR AND CEREBRAL SPINAL FLUID MONITOR/PRESSURE REGULATOR

(71) Applicant: The Regents of the University of Michigan, Ann Arbor, MI (US)

(72) Inventors: Rodney C. Daniels, Plymouth, MI (US); Ashwin Belle, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1085 days.

(21) Appl. No.: 16/765,618

(22) PCT Filed: Nov. 20, 2018

(86) PCT No.: PCT/US2018/062105
§ 371 (c)(1),
(2) Date: May 20, 2020

(87) PCT Pub. No.: WO2019/100074
PCT Pub. Date: May 23, 2019

(65) Prior Publication Data
US 2020/0297982 A1    Sep. 24, 2020

Related U.S. Application Data

(60) Provisional application No. 62/588,548, filed on Nov. 20, 2017.

(51) Int. Cl.
*A61M 27/00*    (2006.01)
*A61B 5/00*    (2006.01)
*A61B 5/03*    (2006.01)

(52) U.S. Cl.
CPC ......... *A61M 27/006* (2013.01); *A61B 5/0022* (2013.01); *A61B 5/031* (2013.01);
(Continued)

(58) Field of Classification Search
CPC .............. A61M 27/006; A61M 27/002; A61M 2205/18; A61M 2205/3337;
(Continued)

(56) References Cited

U.S. PATENT DOCUMENTS

| 6,336,924 B1 | 1/2002 | Lecuyer et al. |
| 2006/0162725 A1 | 7/2006 | Downie |

(Continued)

FOREIGN PATENT DOCUMENTS

| CN | 2614684 Y | 5/2004 |
| CN | 204864499 U | 12/2015 |

(Continued)

OTHER PUBLICATIONS

Huang et al., Prognostic impact of intracranial pressure monitoring after primary decompressive craniectomy for traumatic brain injury, World Neurosurg., 88:59-63 (2016).
(Continued)

*Primary Examiner* — Philip R Wiest
(74) *Attorney, Agent, or Firm* — MARSHALL, GERSTEIN & BORUN LLP (57) ABSTRACT

A dependent closed pressure vessel is fluidly coupled to an independent closed pressure vessel. A pressure sensor monitors pressure in the vessels to generate raw pressure measurement data. A flow meter monitors multidirectional rate of flow of fluid between the vessels and the volume of fluid flowing from the independent closed pressure vessel to generate raw rate of flow and raw volume measurement data. A pressure/flow regulator valve adjusts pressure in the dependent closed pressure vessel in response to a pressure
(Continued)

set point signal generated in response to the raw pressure data, adjusts the rate of flow of fluid between the vessels in response to a rate of flow set point signal generated in response to the raw rate of flow data, and adjusts the rate of flow of fluid between the vessels in response to a volume set point signal generated in response to the raw volume data.

13 Claims, 9 Drawing Sheets

(52) U.S. Cl.
CPC ......... *A61B 5/032* (2013.01); *A61M 2205/18* (2013.01); *A61M 2205/3337* (2013.01); *A61M 2205/3584* (2013.01)

(58) Field of Classification Search
CPC ......... A61M 2205/3584; A61B 5/0022; A61B 5/031; A61B 5/032
See application file for complete search history.

(56) References Cited

U.S. PATENT DOCUMENTS

| | | | |
|---|---|---|---|
| 2011/0275976 A1 | 11/2011 | Negre et al. | |
| 2012/0060622 A1* | 3/2012 | Harris | A61B 5/031 73/861 |
| 2012/0302938 A1* | 11/2012 | Browd | A61M 39/284 604/9 |
| 2014/0083514 A1* | 3/2014 | Ding | G01F 15/046 137/12 |
| 2014/0299206 A1 | 10/2014 | Nagase et al. | |
| 2015/0094644 A1* | 4/2015 | Lenihan | A61M 39/24 604/9 |
| 2016/0331949 A1* | 11/2016 | Lutz | A61M 27/006 |
| 2017/0095649 A1* | 4/2017 | Vase | A61M 27/006 |

FOREIGN PATENT DOCUMENTS

| | | |
|---|---|---|
| WO | WO-2010/141458 A2 | 12/2010 |
| WO | WO-2015/109260 A1 | 7/2015 |
| WO | WO-2015/157320 A1 | 10/2015 |
| WO | WO-2016/059162 A1 | 4/2016 |
| WO | WO-2017/197374 A1 | 11/2017 |

OTHER PUBLICATIONS

International Application No. PCT/US2018/062105, International Search Report and Written Opinion, mailed Mar. 18, 2019.
Johannigman et al., Reducing Secondary Insults in Traumatic Brain Injury, Military Medicine, vol. 180, Issue Suppplement 3, pp. 50-55, Mar. 1, 2015.
Kawoos et al., Advances in Intracranial Pressure Monitoring and Its Significance in Managing Traumatic Brain Injury, Int. J. Mol. Sci., 16(12):28979-97 (2015).
Liu et al., External Ventricular Drains versus Intraparenchymal Intracranial Pressure Monitors in Traumatic Brain Injury: A Prospective Observational Study, World Neurosurg., 83(5):794-800 (2015).
European Patent Application No. 18878776.6, Extended European Search Report, mailed Jun. 25, 2021.
Communication pursuant to Article 94(3) EPC issued in European Patent Application No. 18878776.6 dated Feb. 19, 2024.

* cited by examiner

FIG. 9

DIGITAL EXTERNAL VENTRICULAR DRAIN WITH INTEGRATED INTRACRANIAL PRESSURE MONITOR AND CEREBRAL SPINAL FLUID MONITOR/PRESSURE REGULATOR

FIELD OF THE DISCLOSURE

The present disclosure relates generally to external ventricular drains, and, more particularly, to a digital external ventricular drain device that monitors and regulates intracranial pressure and cerebral spinal fluid flow.

BACKGROUND

It is well-established that accurate intracranial pressure (ICP) monitoring is essential in the evaluation and treatment of traumatic brain injury (TBI), with further evidence that ICP monitoring after primary decompressive craniectomy for TBI patients may significantly decrease in-hospital mortality as well. Furthermore, the use of external ventricular drains (EVDs) in patients with these injuries may also improve survival. During the golden hours (i.e., the time period following traumatic injury during which is the highest likelihood that prompt medical treatment will prevent death), and especially in rapidly changing environments with limited resources, such as during patient transport or in field hospitals, the ability to not only measure ICP but also regulate intracranial pressure while quantifying and regulating the flow of cerebral spinal fluid (CSF) digitally, in real time, with changing patient conditions and position would be invaluable, and this benefit would also extend to the ICU environment in both military and civilian settings. Current EVD systems in clinical use cannot do this as they have no capability to make digital measurements and require manual adjustments by a caregiver for any change in patient position, condition or CSF flow.

The paper, Jay A. Johannigman, USAF MC, et al., *Reducing Secondary Insults in Traumatic Brain Injury*, Military Medicine, Volume 180, Issue suppl_3, Mar. 1, 2015, Pages 50-55, highlighted the challenges in treating TBI patients during rapidly changing clinical settings and throughout multiple echelons of care. It reported that although cared for by an Air Force Critical Care Air Transport Team (CCATT), more than half of the TBI patients who were undergoing air transport had an ICP >20 mm Hg recorded at some point during the flight, with all but one individual showing instances of ICP that were +/−50% of their baseline ICP. The conclusion was that patient movement resulted in changes in ICP from external stimuli and from acceleration/deceleration forces, and that CCATTs should prioritize monitoring, including venting of an intraventricular catheter in real-time if ICP increased above a critical threshold.

SUMMARY

A digital external ventricular drain (DEVD) device that measures and responds to ICP (i.e., opening the EVD flow when pressure meets a predefined threshold) while also quantifying CSF flow rate in real time, and performing both functions concurrently. The DEVD makes adjustments automatically, and in real time, and may alert the caregiver to these changes and make a record of any events occurring, while also transferring this data to a central location as well as to the next team caring for the TBI patient. However, while a digital EVD with basic functional capability exists, this technology is advanced with the disclosed DEVD by including flow regulation for targeting or limiting CSF drainage and by providing backpressure regulation of the DEVD for use when decisions must be made about patient tolerance for removing or internalizing an EVD currently in place. In addition, appropriate closed loop feedback and programming algorithms are provided to enable the pressure and flow valves and sensors to work both together and independently as needed, and include sensors for identifying changes in patient position that the DEVD will be responsive to in real time while also alerting caregivers of these changes.

Furthermore, there is a clear need for the integration of data analytics and predictive modeling in the treatment of TBI from the point of injury through all echelons of care in order to improve outcomes and reduce secondary brain injury, especially as new treatments and interventions become available The present disclosure responds to this need by not only advancing the capabilities of the DEVD device, but enabling the DEVD to interface with a sensor server that will allow the rich digital data streaming from the DEVD (including ICP and CSF flowrate waveform and graphical data) to be utilized in performing data analytics, including the potential for predictive modeling, for advanced TBI diagnosis and treatment in all phases of care. The sensor server will allow data to be securely delivered from the DEVD to a Big Data Platform and will be developed based on best practices, open messaging architecture and open standards. This sensor server will also allow the data from the DEVD to be associated with other waveform and clinical information harvested by the Big Data Platform, such as ECG, arterial pressure waveforms, pulse oximetry, and other clinical information. In this way, as the DEVD is prepared for use in the clinical space, it will also have a ready platform by which the rich digital data it produces can be used in advanced TBI care, and this digital data can then follow the TBI patient from point of injury through the entirety of his/her treatment course.

DETAILED DESCRIPTION

Figure 1:
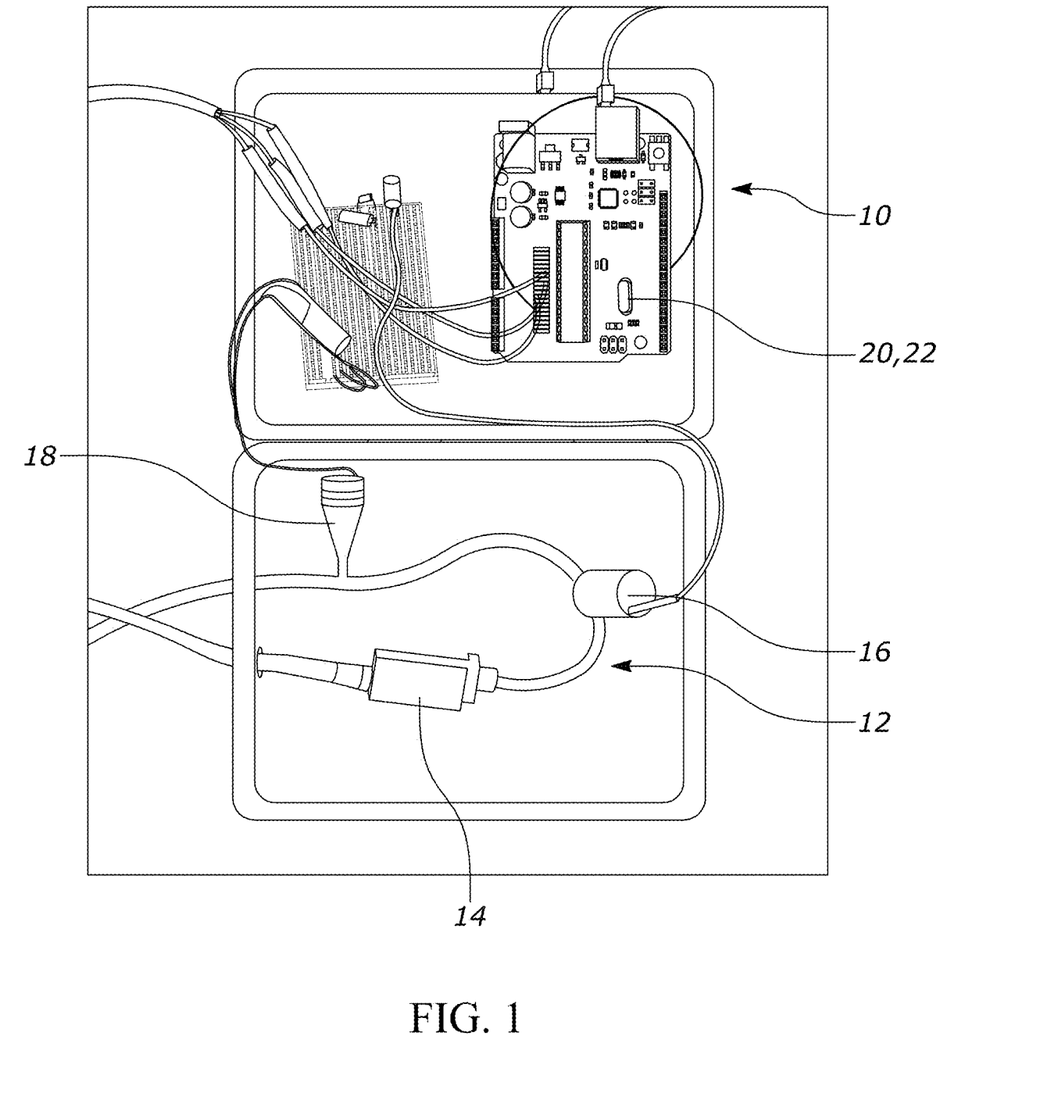
FIG. 1 is an exemplary embodiment of a digital external ventricular drain in a self-contained housing with integrated pressure and flow sensors.
Figure 2:
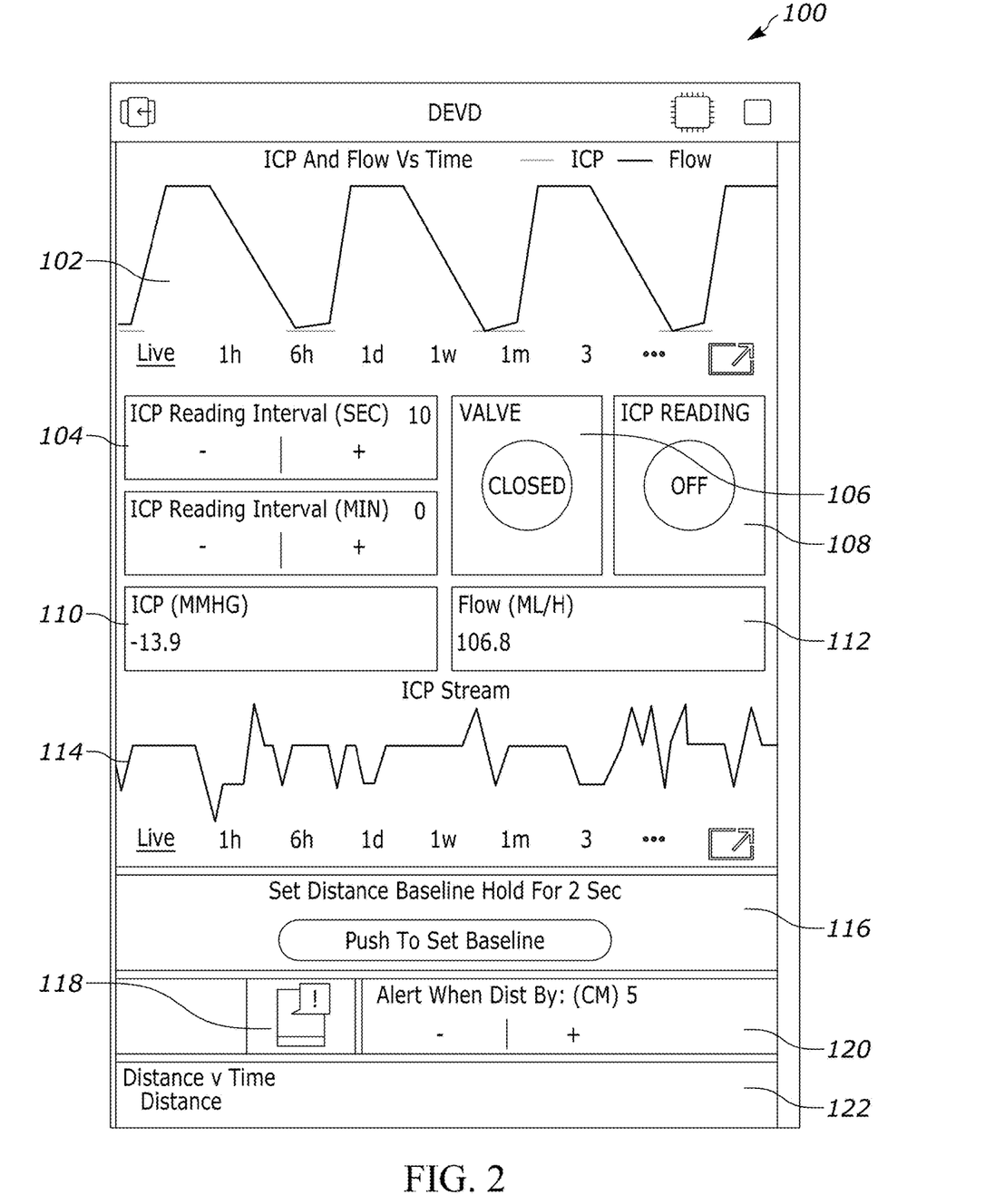
FIG. 2 is an exemplary embodiment of a wireless digital interface reporting pressure and flow data from the digital external ventricular drain of FIG. 1.
Figure 6:
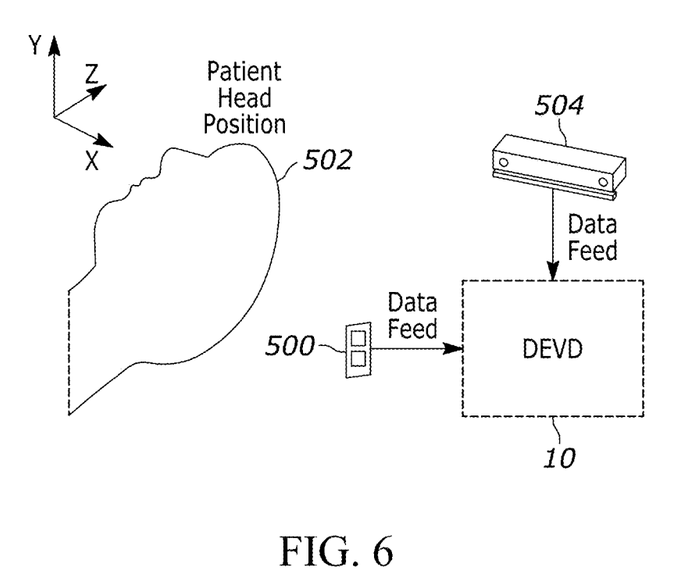
FIG. 6 is an exemplary embodiment of a position sensor in communication with the digital external ventricular drain of FIG. 1 to monitor the position of a patient's head.
Figure 8:
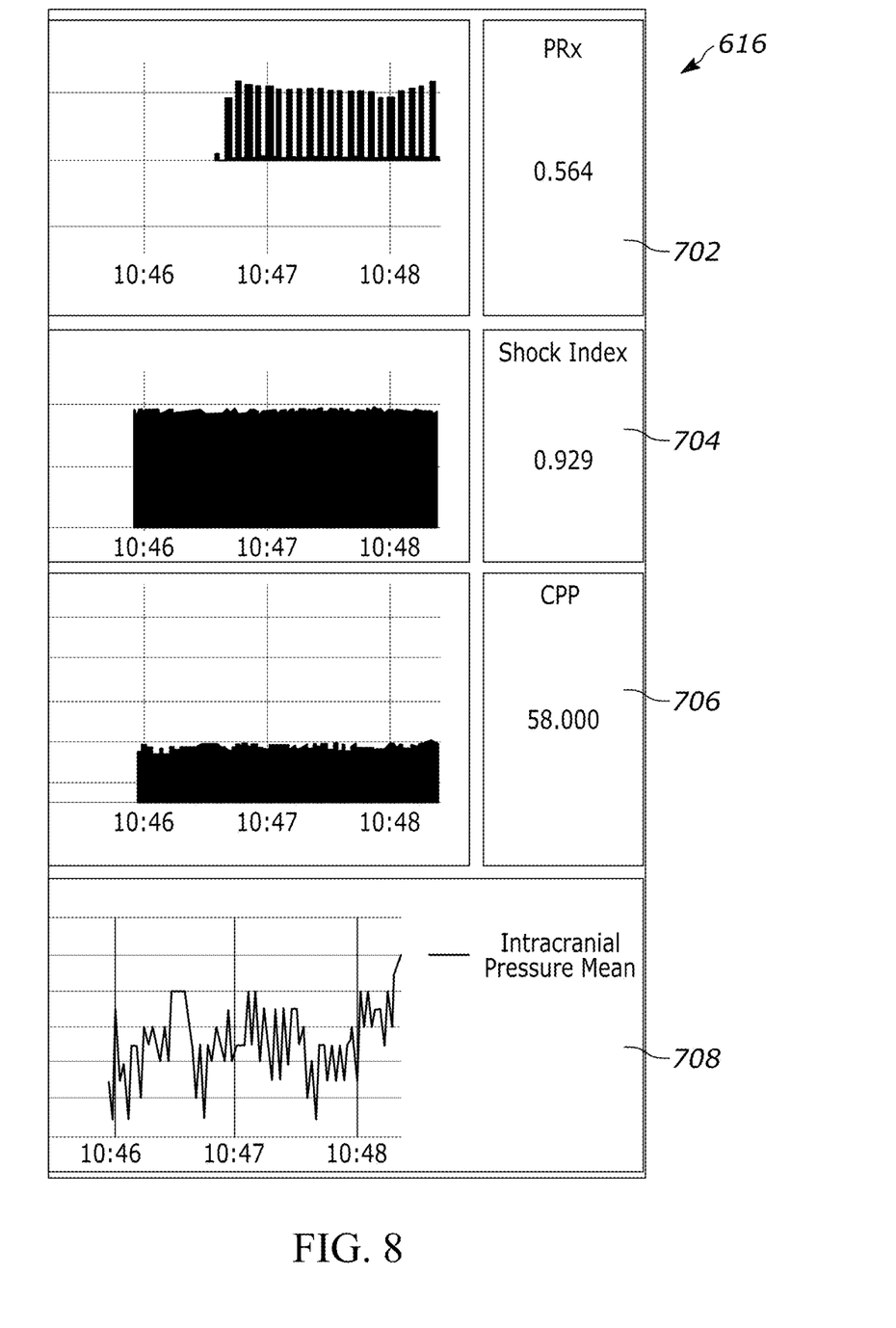
FIG. 8 is an exemplary embodiment of a wireless digital interface reporting metrics on a patient, including integration of other metrics from other sources to show trends, instantaneous values and the severity of either trends or instant values.

Referring to FIG. 1, the pressure feedback system within the Digital EVD 10 works based the principle that there are two closed pressure vessels present: an independent pressure vessel, representing the intracranial/intraventricular space in a patient, and a dependent pressure vessel 12 (the collecting system of the Digital EVD) that is dynamically adjusted to maintain a target pressure and/or flow rate and volume. In its simplest form, the system might be described as a pressure regulation system for liquids that are contained in the two closed vessels, with the added measurement of flow rate and volume between the two vessels (the TBI patient's head and collecting reservoir 12). Therefore, the system 10 includes an integrated pressure sensor/regulator 14, flow sensor 16, and volume regulator 18, with feedback input from a programmable circuit board 20 in order to provide real-time quantification and feedback to the system. Generally, the system 10 includes an upstream pressure sensor 14, a flow/pressure sensor 16 downstream of the upstream pressure sensor 14 to regulate pressure back into the system, and a further downstream sensor 18. This enablers the system to both monitor ICP and CSF flow/volume and to provide active regulation of EVD system pressure and CSF flow rate via feedback loops based on provider input. The "brains" of the regulator system is a minicomputer 20 that monitors pressure, flow, and volume, and adjusts flow and pressure head accordingly, based on changes in patient condition/position and caregiver input. Analog input ports and in-circuit serial programming components are utilized to integrate the components of the system, including the following:

Pressure Sensor(s) 14 in order to monitor pressure in both the independent and dependent pressure vessel (i.e., patient intracranial/intraventricular space and Digital EVD collection chamber);

Flow Meter(s) 16 in order to monitor multi-directional flow between the two pressure vessels;

Volume Meter 18 in order to monitor total volume collected within the collecting chamber;

Digital Pressure/Flow Regulator Valve (not shown) in order to adjust pressure on the dependent pressure vessel side, or in other words, to adjust EVD system backpressure (i.e., adding pressure back into the independent vessel). This regulator valve can also adjust flow as needed;

Patient Position Tracking Sensors in order to continuously monitor patient position and relative changes that could possibly affect CSF flow and pressure (FIG. 6);

Display(s) in order to show data and results from all sensors and controls (FIGS. 2 and 8).

Referring to FIG. 1, these components are integrated into a self-contained device 10 that provides real-time, dynamic response to changing patient position and condition. The Digital EVD 10 is a significant advancement that not only gives caregivers the ability to dial in a targeted pressure level and/or flow rate, but the Digital EVD 10 also provides a significant step forward in safety for patients with TBI and also those with EVDs or externalized shunts by providing continuous monitoring of not only pressure, but also CSF flow rate and total output volume, with integrated alarms for pressure, flow rate, and/or total output volume, determined by caregiver defined parameters based on the patient's underlying diagnosis and clinical condition.

The DEVD 10 enables automatic adjustments with real-time changes in patient position, including immediate EVD venting and increased EVD drainage as required to keep ICP below a critical threshold, and also increases situational awareness of caregivers. This includes alerting caregivers in a busy field hospital or ICU if ICP is increasing and/or if CSF flow is increasing/decreasing as well, and this may help reduce the risk for secondary insults (also referred to as secondary brain injuries) in patients with TBI. Furthermore, the DEVD 10 also addresses a current gap in the medical care of patients who are transitioning between phases of care. Specifically, it enables caregivers in each phase of care to have immediate access to all information prior to that point, whether the events were prior to transport or prior to arrival in the unit or hospital, including historical data regarding ICP and CSF flow. This data also includes documentation of critical time points when pressure and/or flow were outside the range of desired parameters, and enables continuous monitoring and reporting of complex physiological data, such as pressure reactivity index (PrX), via interface with the sensor server that enables integration of DEVD data with other physiologic/monitor data and medical record information. In this way each care team will have the best available information at hand, and may be more aware of the patient's current state and clinical needs, which could improve their ability to care for the patient and potentially reduce morbidity and secondary brain injury.

Further, the DEVD has the ability to: monitor ICP while allowing continuous EVD drainage and monitoring CSF flow rate; set a baseline pressure as defined by the user through a digital interface; identify changes in patient head position that could impact patient care; automatically and in real time adjust the EVD system to maintain the desired EVD pressure and CSF output as necessary based on changes in patient head position and condition, including backpressure if desired; and link wirelessly to caregivers and to a sensor server capable of pushing DEVD data to big data platforms, analytics platforms, and user interfaces, including the ability to call up historical data on demand. The DEVD also alerts the caregiver when pressure or flow is in excess of desired limits set for that patient and automatically adjusts CSF drainage via the DEVD based on patient needs. The DEVD is further integrated with a sensor server to push this data to the platforms described above.

The DEVD includes closed loop controls of pressure and flow parameters (both independently and dependently) based on user input, including the application of system backpressure as needed. Components of the DEVD system include advanced pressure and flow sensors working both in tandem and independently with the ability to monitor ICP during EVD drainage; monitor, quantify, and regulate CSF flow and pressure in a precise manner; and apply EVD system backpressure when desired through programming algorithms run via a programmable interface circuit board and single-board minicomputer.

Therefore, the digital EVD system 10 with integrated ICP monitor and CSF flow monitor/pressure regulator has the ability to:

Report ICP in real-time while concurrently allowing continuous EVD drainage/CSF flow in an automated and intermittent way, and enable user defined time frames for ICP measurement and reporting (e.g., every minute, 5 minutes, 15 minutes, etc. . . . ).

Identify changes in patient head position in real time via one or more of the following sensors that may be integrated together within one master sensor 500 (FIG. 6): (a) an altimeter to determine vertical height accurately within 1 cm, (b) an imaging sensor in order to identify small changes in vertical and/or horizontal position (in multiple planes—x, y, and z), (c) an accelerometer-gyroscope in order to detect and report head movement to the DEVD, and (d) an ultrasonic sensor to identify vertical height and changes in vertical distance.

Automatically adjust to changing patient positions and condition while maintaining user set EVD system pressure and automatically open EVD flow to relieve pressure if ICP rises above a set pressure point.

Alert the caregiver to changes in ICP or CSF drainage, whether above or below defined set points defined by the user and time mark this information for future review.

Quantify the amount of CSF drainage in real time (mL/hr), and cumulatively in user defined collection periods, while controlling flow through fine flow valve adjustments based on user input of targeted flow rate and/or cumulative CSF drainage desired.

Provide EVD system backpressure regulation based on user defined parameters in cases where backpressure is required to test patient readiness for removal of the EVD or in preparation for internalization of an intraventricular shunt (the equivalent of raising an EVD by 10 cm or other set point in current manual EVD systems in order to attain this backpressure).

Report data and graphics wirelessly to portable devices and allow control of the DEVD remotely via this wireless link.

Report historical data regarding points of high/low ICP or CSF flow and keep a record of this data that will follow the patient throughout all phases of care.

Figure 7:
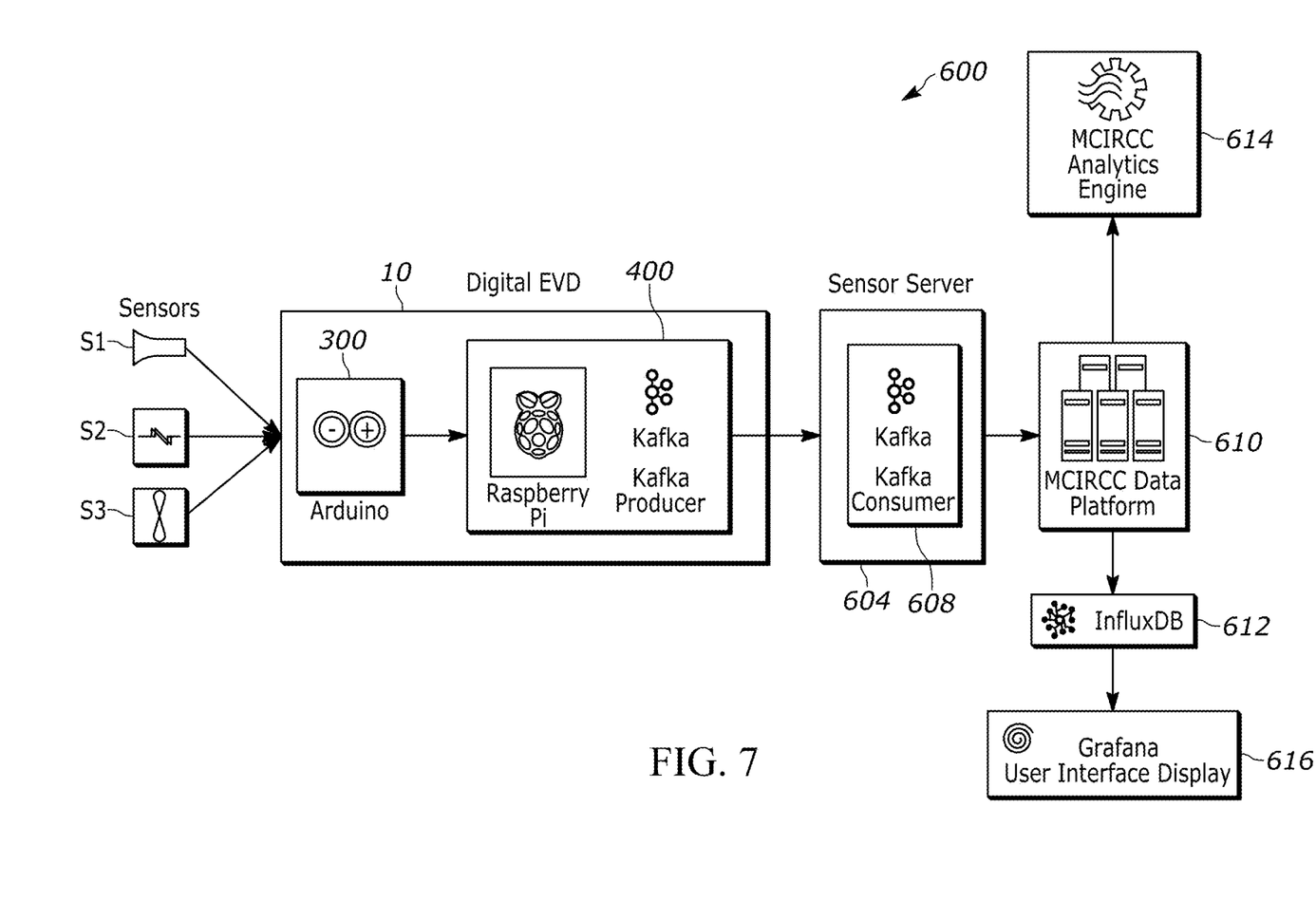
FIG. 7 is an exemplary embodiment of a sensor server integration with data communication proceeding from sensors contained within the digital external ventricular drain of FIG. 1, to the programmable circuit board of FIG. 4 and the single-board computer of FIG. 5 with an integrated real-time data stream publication process, to a sensor server containing real-time data stream subscription process, and on to a Big Data Platform, Analytics Engine, and/or user interface.

Link to a sensor server 608 or similar software interface with open messaging architecture and open standards with the ability to push all data (including waveforms) to big data storage 610 and advanced analytical platforms 614, among others.

Operate portably as a self-contained unit for use in transport or other environments where portability is advantageous.

The DEVD includes connections compatible with the tubing size and material used in current EVD systems and will include a wireless digital interface display (FIG. 2) capable of reporting ICP (in mmHg), current CSF flow rate (in mL/hr), total volume (in mL) over a defined time period, backpressure applied (in cm H2O), graphical data display, alarms for high/low pressure and flow, and the ability to see historical data, as well the capability for a caregiver to input target EVD system parameters, such as ICP maximums/minimums, desired CSF flow rates, and backpressure targets. This is especially important for patients with externalized ventricular shunts who need to maintain a specific set pressure regardless of patient positioning (e.g., 10 cm in height above the tragus on traditional EVD systems). With respect to backpressure regulation (e.g., can the patient tolerate shunt removal?), the system measures how much backpressure to use to test the system and/or automatically adjust to patient movement. In particular, the differential between inputs of upstream pressure and downstream device pressure may indicate there is a position issue with the patient (e.g., patient has moved and it is no longer 10 cm in height above the tragus) or a warning that something is wrong. To test backpressure, the ICP is measured at a steady, low pressure state to act as a baseline measurement. Additional water is added for additional system pressure, and ICP is then measured to test if the patient can tolerate the increase.

Referring to FIG. 2, an embodiment of a graphical user interface 100 that may be generated on a display unit of an external computing device, such as a desktop computer, laptop computer, smartphone, tablet computer, etc. In particular, the external computing device may receive the data via hardline connection or wireless connection from the DEVD 10, and the graphical user interface 100 on the external computing device may generate a display of reports of the ICP data received from the DEVD 10, and further generate a display of controls of how to display the ICP data and/or controls to the DEVD 10. In this embodiment, the graphical user interface 100 is customizable to included one or more of the following: 1) real-time graph 102: plots flow and ICP in real time and may be saved in a data historian; 2) step buttons 104: provide user control over ICP reading interval in seconds and minutes; 3) valve button 106: controls valve OPEN/CLOSE; 4) interval button 108: controls whether or not to read ICP at certain intervals; 5) pressure value display 110: reports ICP in mmHg; 6) flow value display 112: reports flow in mL/hour; 7) waveform graph 114: plots ICP waveform in real time—only turns ON when valve is CLOSED; 8) baseline button 116: sets distance and pressure baseline; 9) push notification 118: notifies user when new data is pushed to the computing device; 10) deviation step button 120: user control over the distance deviation threshold; 11) distance graph: plots distance in real time.

Figure 3:
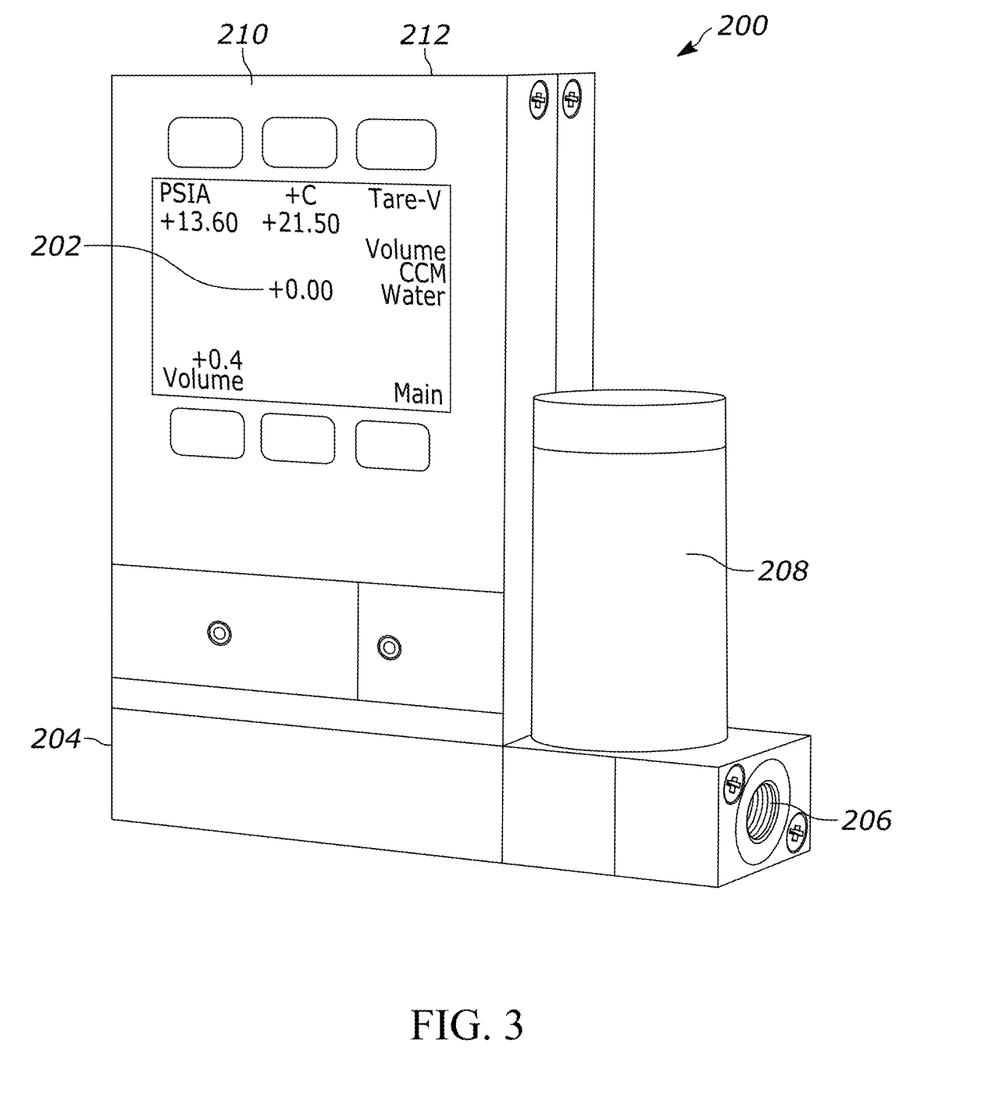
FIG. 3 is an exemplary embodiment of a pressure/flow controller of the digital external ventricular drain of FIG. 1 and controlled through closed loop feedback.
Figure 4:
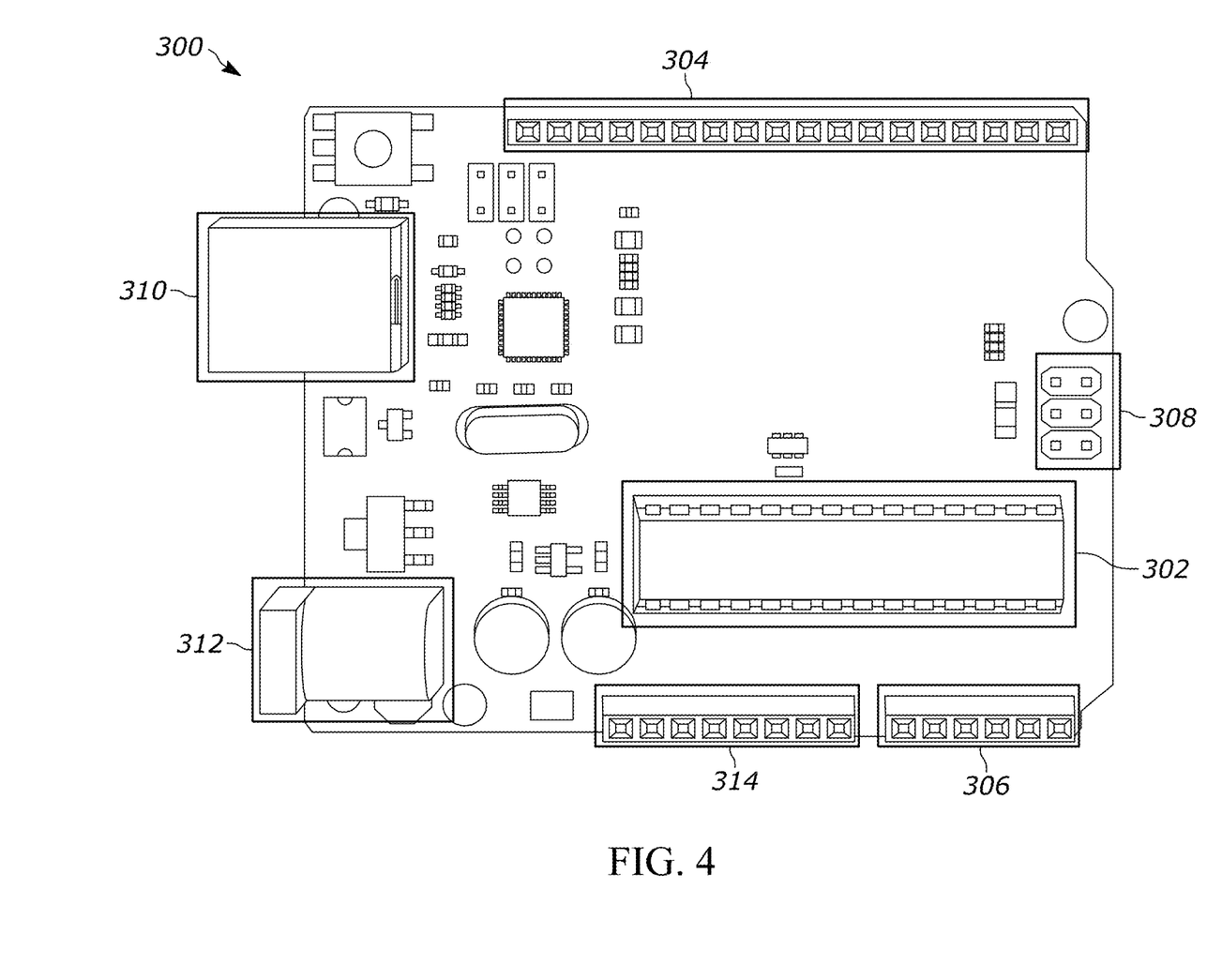
FIG. 4 is an exemplary embodiment of a programmable circuit board to provide feedback regulation of pressure and flow/volume to the digital external ventricular drain of FIG. 1.
Figure 5:
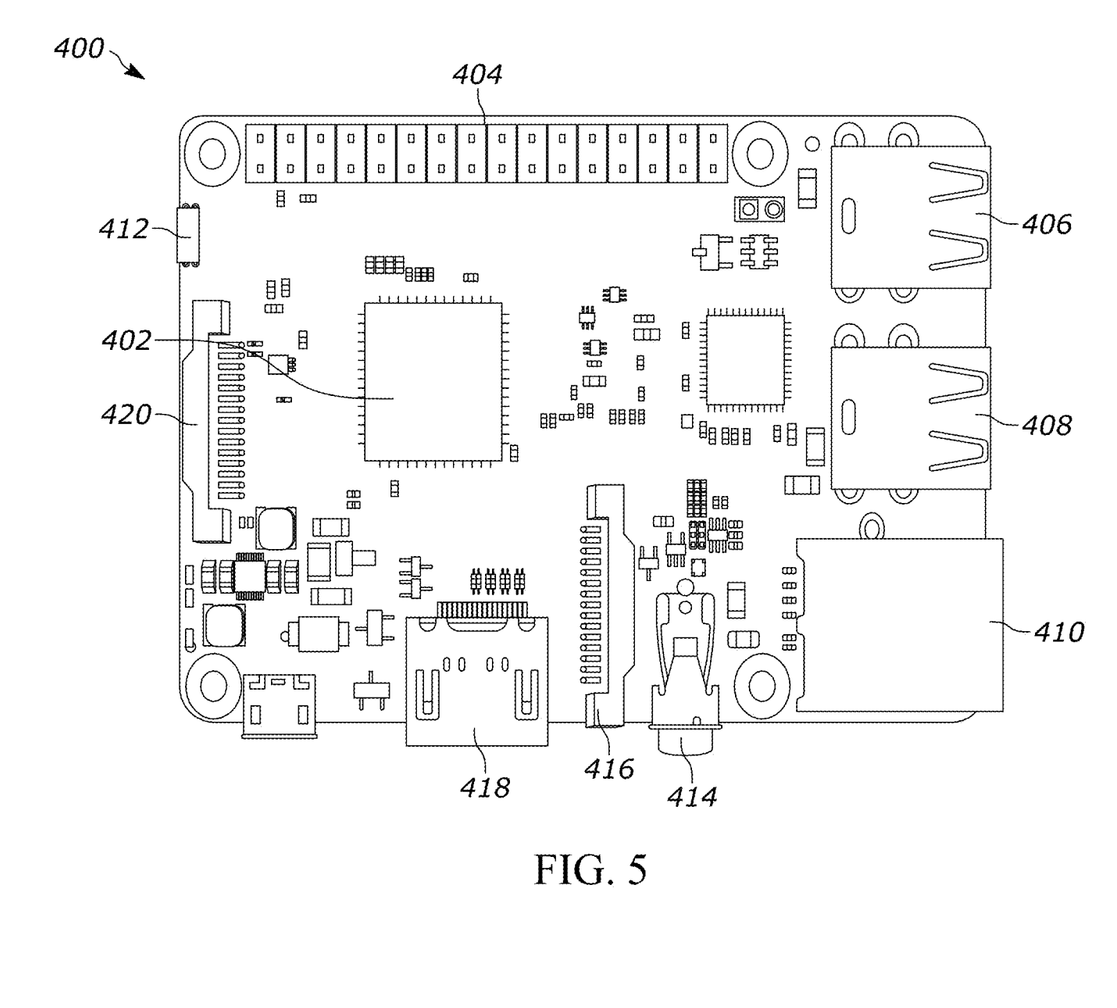
FIG. 5 is an exemplary embodiment of a single-board computer to provide communication with a sensor server and wireless interfacing capabilities.

Referring to FIGS. 3-5, the DEVD components that enable the innovative capabilities of the system include a combination programmable flow sensor/regulator and pressure sensor/regulators, such as the Alicat Scientific™ pressure/flow controller 200 shown in FIG. 3, that works both in tandem and independently with closed loop controls in accordance with the algorithms disclosed below. The combination programmable flow sensor/regulator and pressure sensor/regulator may be used as a single component to replace the individual sensors/regulators 14, 16, 18. In addition, a second pressure/flow controller may be provided upstream or downstream of the pressure/flow controller 200 to enable backpressure manipulation by the DEVD. Integral to these controls is input through a programmable circuit board interface 22 and single-board minicomputer 20, such as, for example, the Arduino® UNO programmable circuit board 300 (FIG. 4) and Raspberry-Pi® single-board minicomputer 400 (FIG. 5), respectively. These interfaces allow the system to communicate with a sensor server in the manner described below and allow for wireless data display on a mobile device as shown in FIG. 2 as well as the capability for caregivers to control the DEVD remotely.

Briefly, referring to FIG. 3, the pressure/flow controller 200, such as the Alicat Scientific™ pressure/flow controller, includes a display interface 202 for programming the pressure/flow controller 200 in order to establish pressure and flow setpoints, and regulate the pressure and flow of the fluid through the controller 200. Fluid flows into the the pressure/flow controller 200 through an inlet connection port 204, and out of the pressure/flow controller 200 via an outlet connection port 206. Sensors internal to the pressure/flow controller 200 measure the rate of flow and the pressure of the fluid as it flows through the device, and regulates the flow and pressure of the fluid out of the outlet connection port 206 in accordance with the programmed setpoints using a control valve 208. In this embodiment, a power jack 210 and communication port 212 are provided on the top of the flow/pressure controller 200, with the communication port 212 transmitting flow and pressure measurements to an external device, such as the programmable circuit board interface 22.

Referring to FIG. 4, the programmable circuit board interface 300, such as the Arduino® UNO programmable circuit board, includes a microcontroller 302, a serial digital output interface 304, and analog input 306, an in-circuit serial programming port 308, a communication port (e.g., Universal Serial Bus) 310, a power input port 312 and a power supply 314. Referring to FIG. 5, the minicomputer 400, such as the Raspberry-Pi® single-board minicomputer, includes a microprocessor 402 and a general purpose input/output (GPIO) interface 404. In addition, the minicomputer 400 includes several communication ports according to different protocols and methods of communication, such as wired and wireless communications. For example, Universal Serial Bus (USB) ports 406, 408, local area network (LAN) ports 410, and wireless interfaces (e.g., Bluetooth™ and WiFi) 412 may be provided. Audio/visual interfaces may also be provided, including, but not limited to, an audio input port 414, a video input port 416, and a video output port (e.g., High-Definition Multimedia Interface) 418, and a display output port 420. External media interfaces, such as a secure data micro card port (not shown), may also be provided. Although the above examples of the programmable circuit board 300 and the minicomputer 400 are "off-the-shelf" items, those of ordinary skill in the art will understand that an alternative device(s) may be utilized, including, but not limited to a custom board that may replace one or both of the programmable circuit board interface 300 and/or the minicomputer 400. For example, the Arduino®/Raspberry-Pi® example above generally utilizes an "ask-and-report" communication protocol with external devices, which may not be fast enough to process and handle streaming ICP waveform data at the standard 125 Hz. Accordingly, if streaming ICP waveform data is desired, the board(s) may be replaced with a board having a faster processor, different communication protocol, etc. that can handle and process data streaming.

Referring to FIG. 6, additional components include hardware designed to identify patient head position, and changes in head position, accurately and in real time utilizing one or more sensors that may be integrated within an array 500 positioned on or near the patient 502. These sensors may include an altimeter which determines vertical height accurately within 1 cm, an image sensor 504 in order to identify small changes in vertical and/or horizontal position (in multiple planes—x, y, and z), an accelerometer-gyroscope capable of reporting head movement to the DEVD, and/or an ultrasonic sensor capable of identifying vertical height and changes in vertical distance. All these sensors may integrate with the DEVD system 10 and the sensor server. Upon calibrating the pressure sensors to atmospheric pressure and aligning the DEVD at a height equal to the patient's tragus (which is at approximately the same vertical position as the patient's cerebral ventricles) or other external anatomic mark, the DEVD 10 automatically adjusts pressure in the DEVD and/or flow rate in response to changes in head position, particularly changes beyond a particular threshold (e.g., more than 1 cm), to keep the patient's ICP below a critical threshold or at some other setpoint pressure/flow. Alternatively, or in addition, the DEVD 10 may notify caregivers of the change in the patient's head position.

The DEVD 10 enables automatic adjustments with real-time changes in patient position, including immediate EVD venting and increased EVD drainage as required to keep ICP below a critical threshold, and also increases situational awareness of caregivers There are several hardware and software components that work together to make the Digital EVD a complete solution and enable sensor server integration with open architecture. Briefly described below are the components of both the DEVD 10 and the sensor server that make this integration possible and manage the transfer of DEVD data to big data and advanced analytic platforms throughout all echelons of care.

Referring to FIG. 7, the Digital EVD component 10 includes the programmable circuit board 300, the single-board minicomputer 400, and software running on both. The single-board minicomputer 400 continuously acquires raw measurement from the sensors S1, S2, S3 via a persistent serial communication channel between the programmable circuit board interface and single-board minicomputer 400, where sensors S1, S2, S3 may be any combination of the integrated pressure sensor/regulator 14, flow sensor 16, volume regulator 18, pressure/flow controller 200, optional backpressure/flow controller and/or position sensor 500, 504. The single-board minicomputer 400 then relays the acquired measurements to a real-time data stream publication process 602, such as a Kafka™ Producer, that resides on the single-board minicomputer 400. Kafka™ is an open source software messaging package that creates data pipelines that are scalable. The real-time data stream publication process encodes and encrypts the messages and then publishes them to all to a real-time data stream subscription process that resides on the sensor server 604, such as a Kafka™ Consumer, that has a registered interest in the messages.

The sensor server 604 receives data from any device, aggregates it, and sends it off to the proper storage or analytics mechanism. The sensor server 604 includes a tuned real-time data stream subscription process 608, such as the Kafka™ Consumer, that subscribes to messages from any of the DEVDs 10 that are monitoring patients. The subscription process 608 can then route messages to any end point within a Big Data Platform 610. Data from the DEVDs may also be routed to a time-series database 612 (e.g., InfluxDB). However, data could also be routed to other storage systems like Hadoop® by Apache™, Netezza® by IMB®, a regular file system, or even sent into an Analytics Engine 614. In this way, the DEVD data can be integrated with other physiologic and medical record data in order to perform advanced analytics that may improve diagnostic capabilities and identify pending clinical deterioration well before they occur. In addition, a visualization dashboard 616, an example of which is shown in FIG. 8 as created in a tool called Grafana® by Grafana Labs, allows clinicians to see metrics on each monitored patient wirelessly (e.g., pressure reactivity index (PRx) 702, cerebral blood flow 706, etc.), and interact remotely if desired. In addition, integration of other metrics from other sources may be monitored, such as a shock index 704 of how the patient is doing hemodynamically (e.g., heart rate, blood pressure). The visualization dashboard may display trends 708 (granular) and/or instantaneous (current) values for each metric, as well as an indication of severity in the trends and/or instantaneous values.

The DEVD 10 with sensor server 604 integration also allows scaling throughout the hospital or other medical facility. In addition, it enables the capability to monitor a TBI patient's progress throughout all transitions of care, from either a central location, via remote access, and/or wirelessly between transitions of care in which care givers must have vital clinical information at hand.

Figure 9:
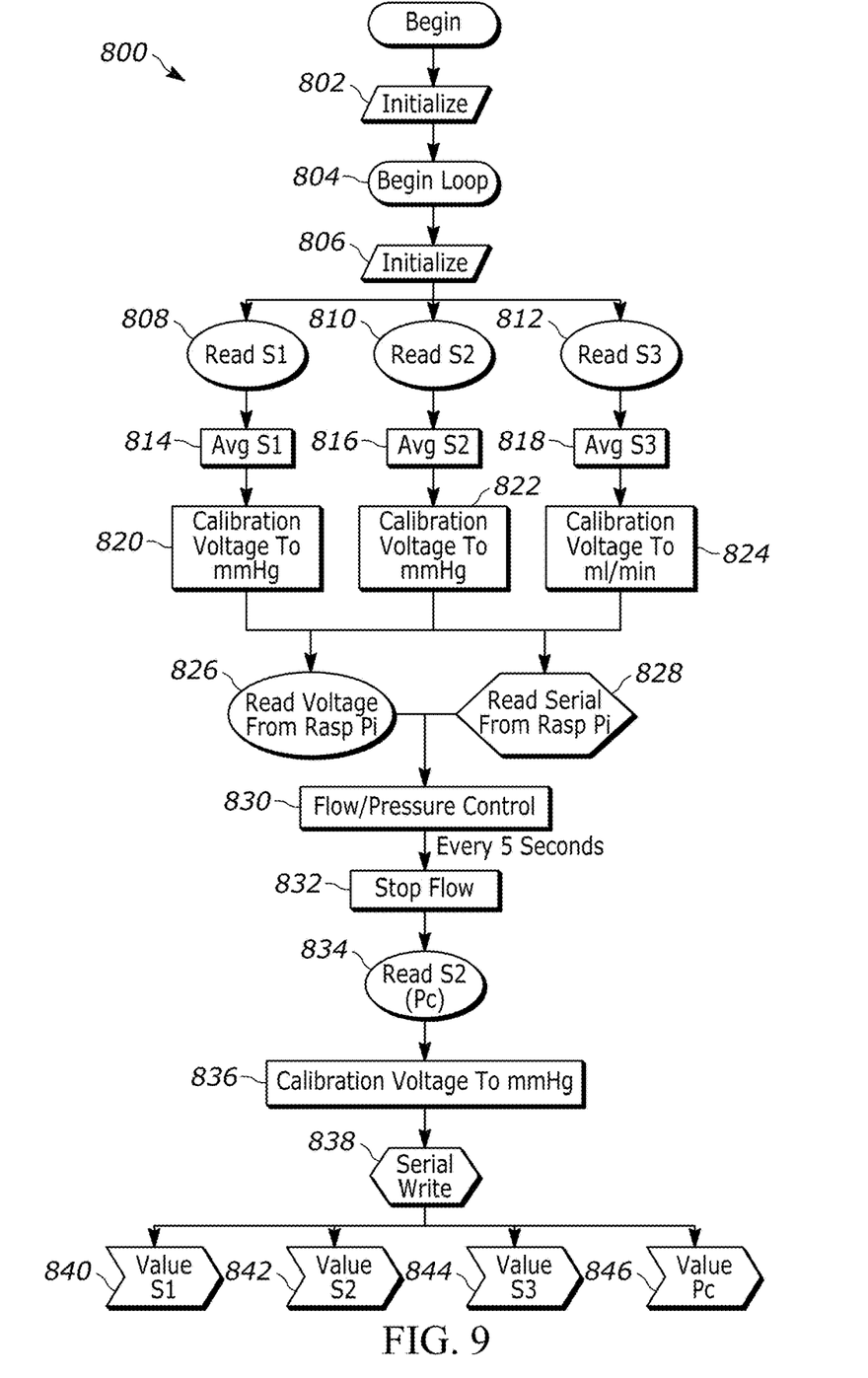
FIG. 9 is an exemplary embodiment of a closed loop control of pressure and flow parameters in the digital external ventricular drain that may be executed by the programmable circuit board of FIG. 4.

FIG. 9 is a flowchart of a closed loop control of pressure and flow parameters. In general, the control loop communicates with the pressure and flow sensors continuously or near-continuously as the sensors produce measurement data for pressure and flow rate. Once the programmable circuit board of FIG. 4 is instantiated at block 802, the control loop may begin at block 804, and each of the pressure and flow sensors may be initialized at block 806 for the programmable circuit board to communicate with the sensors in real time as the sensors produce raw measurement data. In an embodiment, each of the sensors (S1-S3) have a high rate of data production and are read simultaneously at blocks 808, 810, 812. Periodically, the raw measurement data from each sensor may be averaged by a voltage value determined at blocks 814, 816, 818 and calibrated to the averaged raw measurement data at blocks 820, 822, 824. In an embodiment, the voltage value corresponds to a particular pressure (mmHg) or flow value (ml/min), as established by a lookup table from the manufacturer of the sensor.

The voltage values are received by the single-board computer 400, such as the Raspberry Pi computer of FIG. 5, and read from the single-board computer 400 by the data stream publication process 602 at blocks 826, 828 for transmission to the sensor server 604 and other processes, such as the Kafka™ Consumer 608, Big Data Platform 610, time-series database 612 or other storage systems 614, for further control and analytics. In one embodiment, the voltage values, which are read as pressure and flow values, are provided to a mobile computing device running an application, such as that shown in FIGS. 2 and 8, for monitoring the pressure and fluid flow including instantaneous pressure and fluid flow, trends, severity, etc. These applications may also establish pressure and fluid flow set points for transmission to the DEVD 10, such as backpressure control to ensure intracranial pressure. Additionally, the serial values for real time raw measurements data of the pressure and flow are read from the single-board computer 400, with control signals sent back for on/off control of the sensors at block 830.

In addition to reading pressure and fluid flow values from the DEVD, the closed loop control may maintain the pressure and flow at a constant set point value for cranial pressure and spinal fluid flow at blocks 832-838. In one embodiment, backpressure may be measured in order to test the patient for reaction to shunt removal. In particular, the backpressure cannot be measured accurately while there is flow, so control is provided to the pressure/flow regulator valve to stop fluid flow at block 832. This may be done periodically (e.g., every 5 seconds), which may be changed based on clinical needs. Then the absolute cranial pressure may be read at block 834, a voltage value calibrated to the absolute pressure measurement at block 836, similar to the calibration disclosed above, and a serial write made to the single-board computer 400 at block 838 for transmission to, for example, the mobile computing device at blocks 840-846.

The DEVD 10 establishes communication with a sensor server 604 capable of providing real-time retrieval of historical data and transmission of DEVD data to big data platforms 610, advanced analytic engines 614, and wireless interactive displays 616. In order to truly advance the capabilities of the DEVD 10, communication between the DEVD 10 and a sensor server 604 capable of pushing all data is established, including graphical and waveform data, to the big data platform 610, advanced analytics platform 614, and to a user interface 616 that will enable visualization of this data remotely and wirelessly while allowing caregiver input to define the pressure and flow parameters required for each individual wounded warrior or TBI patient. This system also allows for transfer of vital patient data between transitions and through all echelons of care from the field hospital or outside facility, through transport, and to a definitive care facility. As noted above, this will include the integration of the publication process 602 within the single-board minicomputer 400 that will link with the subscription process 608 residing on the sensor server 604. This subscription process 608 is programmed to route messages (data) to any end point within the Big Data Platform 610. Additionally, data is routed from the DEVD 10 to a time-series database 612 (e.g., InfluxDB) for further delivery to a user interface display 616 (e.g., Grafana®). This data will also be considered for routing to other storage systems including Hadoop®, Netezza®, or a regular file system. Finally, a pathway is established for this data to be sent into the Analytics Engine 614 so that this vital patient data can be combined with other physiologic and clinical data for future work in developing predictive analytics and advanced diagnostic capabilities to support future precision medicine approaches.

After completing bench testing and initial sensor server integration, the DEVD may be tested in realistic clinical conditions via an established model of swine traumatic brain injury. In this model, traumatic brain injury is simulated by introducing an expanding fluid filled balloon into one cerebral hemisphere which mimics an expanding hematoma on that side. A standard ICP monitor is placed and ICP is recorded throughout the experiment, along with continuous physiologic monitoring and laboratory measures, including blood gas measurements. Cerebral perfusion pressures will be calculated and recorded as well. The DEVD will be integrated with an intraventricular catheter placed by the animal laboratory technicians, and ICP, as well as CSF flow rate and EVD system pressure, will be monitored by the DEVD as ICP increases and the TBI model progresses. In addition, Digital EVD target pressure and flow parameters will be adjusted and observed for appropriate effect, including the application of backpressure from the DEVD. Intracranial pressure measurements via the DEVD will be compared with the current standardized ICP monitor used for the swine TBI model, and flow/volume measurements will be confirmed via direct measurements of volume and flow rate of CSF obtained in the collecting reservoir of the system.

This solution provides caregivers from the field hospital, to the ICU, to the rehab facility, the ability to quantify, regulate, and monitor ICP and CSF drainage remotely in a manner that was previous unavailable as well as link vital patient data regarding ICP and CSF flow to visual interfaces and data storage that can be accessed at any time and provide platforms for advanced analytics and precision medicine. Given the importance of both ICP monitoring and EVD use in TBI, this DEVD system provides a safety net for caregivers who are operating with limited resources or caring for multiple patients, and would also improve the accuracy of pressure and flow measurements obtained via EVDs. Furthermore, this system alerts the caregiver to changes in ICP or CSF flow and keep a historical record of these changes, while having the capability to create backpressure, automatically respond to changing patient conditions, and regulate flow in a precise manner to ensure excessive CSF loss does not inadvertently occur. This is especially important in cases where large swings in CSF drainage and ICP can lead to clinical deterioration, electrolyte disturbances, and increased adverse outcomes such as secondary brain injury.

The DEVD device may be utilized in any environment in which ICP monitoring is being conducted and/or CSF drainage is being tracked, quantified, or evaluated. The device may be used immediately after insertion of an EVD or intraventricular catheter, and given that it offers real-time measurements and adjustments in EVD pressure and flow parameters with changing patient position and condition, the device could have a significant impact on the ability of providers to care for these patients, including a decrease in caregiver workload while increasing situational awareness. Because the device can be used immediately after EVD/catheter placement, it could be utilized early in patient care, from the field hospital to the civilian ICU, as well as during the transport of brain injured patients with an EVD, ICP monitor, or catheter in place. Furthermore, with the integrated open source architecture for data transfer and its ability to link up with a sensor server, critical patient data regarding ICP and CSF flow could be communicated across all echelons of care, with each new caregiver having immediate access to historical data and graphical information regarding vital clinical information, from the field hospital or outside institution, through transport, to level IV or higher definitive care and tertiary/quaternary care centers. In addition, the use of the DEVD could extend to other patients as well, such as those who require externalization of a shunt for hydrocephalus in which fine adjustments in EVD system pressure are required and continuous quantification and measurement of CSF drainage is essential, with clinical progression tracked, monitored, and recorded via sensor server integration.

Given the multiple settings in which the DEVD can be used, users would include nurses, mid-level providers, and physicians involved in the care of the brain injured patient as well as paramedics, combat medics, and others who are involved in patient transport.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed is:

1. A device comprising:
    a dependent closed pressure vessel adapted to fluidly couple to an independent closed pressure vessel and adapted to collect fluid from the independent closed pressure vessel;
    a computing device;
    a pressure sensor operatively coupled to the computing device and adapted to monitor pressure in the independent closed pressure vessel and in the dependent closed pressure vessel, adapted to generate raw pressure measurement data from the monitored pressure and adapted to provide the raw pressure measurement data to the computing device; and
    a flow/pressure sensor downstream of the pressure sensor, with the dependent closed pressure vessel extending between the pressure sensor and the flow/pressure sensor, and operatively coupled to the computing device and adapted for monitoring multidirectional rate of flow of fluid between the independent closed pressure vessel and the dependent closed pressure vessel, adapted for measuring a volume of fluid flowing from the independent closed pressure vessel, adapted to generate raw data from which a rate of flow and a volume measurement data are determined, and adapted to provide the rate of flow and volume measurement data to the computing device;
    wherein the computing device is adapted to generate a pressure set point signal in response to the raw pressure measurement data, adapted to generate a rate of flow set point signal in response to the rate of flow measurement data, and adapted to generate a volume set point signal in response to the volume measurement data,
    the device further comprising a pressure/flow regulator valve operatively coupled to the computing device and adapted to adjust pressure in the dependent closed pressure vessel in response to the pressure set point signal, adapted to adjust the rate of flow of fluid between the independent closed pressure vessel and the dependent closed pressure vessel in response to the rate of flow set point signal, and adapted to adjust the rate of flow of fluid between the independent closed pressure vessel and the dependent closed pressure vessel in response to the volume set point signal.

2. The device of claim 1, wherein the dependent closed pressure vessel is adapted to fluidly couple to the independent closed pressure vessel via an intraventricular catheter.

3. The device of claim 1, wherein the dependent closed pressure vessel is adapted to fluidly couple to the independent closed pressure vessel via an external ventricular drain.

4. The device of claim 1, wherein the dependent closed pressure vessel is a collecting reservoir for cerebral spinal fluid from the independent closed pressure vessel.

5. The device of claim 1, wherein the independent closed pressure vessel is an intracranial/intraventricular space within a brain of a person, the pressure in the independent closed pressure vessel is intracranial pressure, and the fluid is cerebral spinal fluid.

6. The device of claim 1, wherein the computing device is further adapted to automatically adjust the pressure set point signal in response to raw pressure measurement data from the pressure sensor when the pressure on the dependent closed pressure vessel meets a predefined threshold.

7. The device of claim 1, wherein the computing device is further adapted to automatically adjust the rate of flow set point signal in response to a raw rate of flow measurement data from the flow/pressure sensor when the rate of flow of fluid meets a predefined threshold.

8. The device of claim 1, wherein the computing device is further adapted to automatically adjust the rate of flow set point signal in response to a raw volume measurement data from the flow/pressure sensor when the fluid volume meets a predefined threshold.

9. The device of claim 1, wherein the computing device is further adapted to adjust the pressure set point signal in response to a user defined pressure input, adjust the rate of flow set point signal in response to a user defined rate of flow input, and adjust the rate of flow set point signal in response to a user defined volume input.

10. The device of claim 1, wherein the computing device comprises a real-time stream publication process to encode and encrypt messages with the raw measurement data from the pressure sensor and flow meter, and publish the messages to a subscription process.

11. The device of claim 1, wherein the dependent closed pressure vessel, pressure sensor, flow meter, computing device, and pressure/flow regulator value are integrated.

12. The device of claim 1, further comprising:
    a sensor operatively coupled to the computing device and positioned on or proximate to the independent closed pressure vessel, the sensor adapted to monitor a position of the independent closed pressure vessel in at least a two-dimensional space, and adapted to provide data on the position of the independent pressure vessel to the computing device.

13. The device of claim 12, wherein the sensor comprises one or more of the following: an altimeter, an accelerometer-gyroscope, and three dimensional positioning sensor.

\* \* \* \* \*

UNITED STATES PATENT AND TRADEMARK OFFICE
CERTIFICATE OF CORRECTION

| | | |
|---|---|---|
| PATENT NO. | : 12,109,378 B2 | Page 1 of 1 |
| APPLICATION NO. | : 16/765618 | |
| DATED | : October 8, 2024 | |
| INVENTOR(S) | : Daniels et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1176 days.

Signed and Sealed this
Sixth Day of May, 2025

Coke Morgan Stewart
*Acting Director of the United States Patent and Trademark Office*